United States Patent [19]

Dalla Betta et al.

[11] Patent Number: 5,314,828
[45] Date of Patent: May 24, 1994

[54] $NO_x$ SENSOR AND PROCESS FOR DETECTING $NO_x$

[75] Inventors: Ralph A. Dalla Betta, Mountain View; David R. Sheridan, Menlo Park, both of Calif.; Daniel L. Reed, Boulder, Colo.

[73] Assignee: Catalytica, Inc., Mountain View, Calif.

[21] Appl. No.: 536,895

[22] Filed: Jun. 12, 1990

[51] Int. Cl.⁵ .................... G01N 25/22; G01N 27/50; G01N 25/20
[52] U.S. Cl. ...................................... 436/118; 422/51; 422/83; 422/177; 436/116; 436/137; 436/143
[58] Field of Search ............... 436/116, 118, 137, 143, 436/147, 159; 422/83, 94-98, 51, 56, 52, 177, 168; 55/74, 387

[56] References Cited

U.S. PATENT DOCUMENTS

| | | |
|---|---|---|
| 2,298,288 | 1/1974 | Gerrish et al. ............... 436/137 X |
| 2,751,281 | 6/1956 | Cohn ............................ 436/147 X |
| 2,916,358 | 12/1959 | Valentine et al. ............ 436/147 X |
| 3,460,909 | 8/1969 | Gayle ............................ 422/96 |
| 3,476,517 | 11/1969 | Smith ............................ 422/96 |
| 3,488,155 | 1/1970 | Ayers ............................ 436/147 |
| 3,522,010 | 7/1970 | Archer .......................... 422/96 |
| 3,537,823 | 11/1970 | Innes ............................. 436/147 |
| 3,540,851 | 11/1970 | Vree et al. .................... 436/117 |
| 3,547,587 | 12/1970 | Innes ............................. 436/147 |
| 3,586,486 | 6/1971 | Kim et al. ..................... 422/97 |
| 3,599,427 | 8/1971 | Jones et al. ................... 60/274 |
| 3,607,084 | 9/1971 | Mackey et al. ............... 436/152 |
| 3,725,005 | 4/1973 | Innes ............................. 436/147 |
| 3,791,936 | 2/1974 | Pebler et al. ................. 204/153.18 |
| 3,906,721 | 9/1975 | Micheli et al. ............... 422/95 |
| 3,967,933 | 7/1976 | Etess et al. ................... 436/118 |
| 4,005,001 | 1/1977 | Pebler .......................... 204/426 |
| 4,029,472 | 6/1977 | Micheli et al. ............... 422/95 |
| 4,063,898 | 12/1977 | Fisher .......................... 422/94 |

(List continued on next page.)

FOREIGN PATENT DOCUMENTS 0257842 3/1987 European Pat. Off. .
83-719785/30 of 0000 Japan .
2066963 of 0000 United Kingdom .

OTHER PUBLICATIONS

Catchpole et al., "Dimensionless Groups" I & EC 58(3):46-60 (1960).
Arai et al. "Opt. Detect. Nit. Mon. Metal Porphine . . . Film", *Chem. Letters*, the Chem. Soc. Japan, pp. 521-524, (1988).
"Removal of Nitric Oxide from Exhaust Gas with Cyanuric Acid" Siebers et al. *Combustion and Flame* 79:31-46 (1990).
"Model for a Temperature Dependence . . . by $NH_3$ Fresh Catalyst" Nam et al. *Ind. Eng. Chem. Prod. Res. and Devel.*, (1986) 25:186-192.
"Cyanuric Acid . . . and the effects of Oxygen" Wickie et al., *Combustion and Flame*, 78:249-255 (1989).
"The activity of supported vanadium . . . the selective reduction of NO with ammonia" by Bosch et al. *Applied Catalysis* 29:239-248 (1986).
"Lithium-Vanadium Bronzes . . . Selective Reduction of Nitric Oxide" *Catalysis Today* 4:139-154 (1989).
"Catalytic Reduction . . . on Vanadium Oxide and Iron-Chromium Oxide" *Ind. Eng. Chem. Prod. Res. Devel.*, 14:268-273.

*Primary Examiner*—Robert J. Warden
*Assistant Examiner*—Ramon Torres
*Attorney, Agent, or Firm*—Morrison & Foerster

[57] ABSTRACT

This invention is a process for detecting low levels of nitrogen oxides ($NO_x$) in a flowing gas stream (typically an exhaust gas stream) and a catalytic $NO_x$ sensor which may be used in that process.

22 Claims, 5 Drawing Sheets

U.S. PATENT DOCUMENTS

| | | | |
|---|---|---|---|
| 4,115,067 | 9/1978 | Lyshkow | 422/56 |
| 4,129,848 | 12/1978 | Frank et al. | 338/308 |
| 4,141,955 | 2/1979 | Obiaya | 422/95 |
| 4,170,455 | 10/1979 | Henrie | 422/94 X |
| 4,188,190 | 2/1980 | Muraki et al. | 436/55 |
| 4,236,895 | 12/1980 | Stahl | 436/116 |
| 4,257,777 | 3/1981 | Dymond et al. | 436/116 |
| 4,298,574 | 11/1981 | Bohl | 422/97 |
| 4,305,724 | 12/1981 | Micko | 436/156 |
| 4,315,753 | 2/1982 | Bruckenstein et al. | 436/118 |
| 4,325,912 | 4/1982 | Sawa et al. | 422/95 |
| 4,328,780 | 5/1982 | Andrew | 436/137 X |
| 4,343,768 | 8/1982 | Kimura | 422/97 |
| 4,355,056 | 10/1982 | Dalla Betta et al. | 427/126.4 |
| 4,473,536 | 9/1984 | Carberg et al. | 423/239 |
| 4,473,537 | 9/1984 | Ford et al. | 436/118 X |
| 4,647,777 | 3/1987 | Meyer | 250/339 |
| 4,731,231 | 3/1988 | Perry | 423/235 |
| 4,778,764 | 10/1988 | Fine | 436/116 |
| 4,822,564 | 4/1989 | Howard | 422/52 |
| 4,835,108 | 5/1989 | Cooper | 436/137 |
| 4,836,012 | 6/1989 | Doty et al. | 73/31.06 |
| 4,840,913 | 6/1989 | Logothetis et al. | 436/116 |
| 4,861,567 | 8/1989 | Heap et al. | 423/235 |
| 4,861,979 | 8/1989 | Tardy et al. | 250/227.24 |

$NO_x$ SENSOR AND PROCESS FOR DETECTING $NO_x$

FIELD OF THE INVENTION

This invention is a process for detecting low concentration levels of nitrogen oxides ($NO_x$) in a flowing gas stream (typically a combustion exhaust gas stream) and a catalytic $NO_x$ sensor which may be used in that process.

BACKGROUND OF THE INVENTION

Exhaust gases produced by burning fuels using air as the source of oxidant typically contain small but significant amounts of various nitrogen oxides (NO, $NO_2$, $N_2O_3$, etc.) collectively and interchangeably known as $NO_x$. $NO_x$ is a participant in the photochemical reaction creating modern "smog" and, therefore, is undesirable.

There are a number of ways in which the $NO_2$ may be removed, treated, or even its initial synthesis prevented; however, each such process strongly benefits from use of an accurate monitor for detecting low levels of $NO_x$. The detector may be used in a variety of processes, e.g., closed-loop procedures controlling one or more reaction parameters (such as catalyst temperature, $NO_x$ reductant concentration, or exhaust gas recirculation) all based on $NO_x$ concentration.

There are, however, few low level $NO_x$ sensors available which are practically suitable for inclusion in closed-loop controllers. A major problem of the prior measurement devices has been the lack of sensitivity. An ability to measure $NO_x$ content in combustion gases below 150 ppm with some accuracy is desirable. The major currently available on-line $NO_x$ process analyzers capable of measuring low levels of $NO_x$ are the chemiluminescent analyzers. Such analyzers are expensive, require extensive pretreatment of the gas to be analyzed, and historically have proven to be high maintenance devices. The accuracy of many $NO_x$ sensors, including chemiluminescent sensors, suffer because of interference from other gases which may be found in a combustion gas stream, e.g., $SO_2$, CO, $H_2$, $H_2O$, and various hydrocarbons.

There are a number of methods known for detecting $NO_x$ in flowing gas streams. Perhaps the most well-known of the processes currently used involve the chemiluminescent reaction of nitric oxide and ozone. Ozone is highly reactive and often raises reactivity problems with analyzer components, e.g., O-rings, metals used in the analyzer, and the like. The process operates by the reaction of injected ozone and the nitric oxide in a sample within a reaction chamber having a transmissive window through which the light produced by the chemiluminescent reaction is monitored by a detector. The window in the reaction chamber must be kept clean to maintain analyzer sensitivity and calibration. Water causes substantial problems in these devices. Typical apparatus used in this process may be found in U.S. Pat. Nos. 3,967,933 to Etess et al.; 4,236,895 to Stahl; 4,257,777 to Dymond; 4,315,753 to Bruckenstein et al.; and 4,822,564 to Howard. The use of a chemiluminescent nitrogen oxide monitor device in controlling a nitrogen oxide removal unit the outlet of a boiler is shown in U.S. Pat. No. 4,188,190 to Muraki et al. The devices and processes disclosed herein could be substituted for the nitrogen oxide analyzers shown in Muraki et al.

Another procedure involves the use of an infrared beam, detector, and a comparator chamber. In U.S. Pat. No. 4,647,777 to Meyer a beam of infrared light is passed through a gas sample and into a selective infrared detector. The beam is split and one portion passes through a chamber containing a fluid which absorbs the spectral wavelengths of the selected gas. The two beams are compared and the difference between the two beams gives an indication of the amount of selected gas in the sample. Although such instruments can measure NO and $NO_2$, they suffer from the same shortcomings as do the chemiluminescent analyzers in that they require clean optical surfaces, significant sample pretreatment, and have high maintenance requirements.

U.S. Pat. No. 4,836,012 to Doty et al. shows a semiconductor device made up of a photovoltage cell which, upon exposure to light, develops a voltage or current which varies as a function of the type of gas sorbed. The device requires a "thin light-transmitting gas-absorbing metal Schottkey layer having electrical properties which vary with the type of gas absorbed". Detection of CO, hydrocarbon, water vapor, etc. is suggested; detection of NO is not.

Other methods of determining the trace elements of $NO_x$ which may be present in a gas stream are known. For instance, U.S. Pat. No. 3,540,851 to Vree et al. suggests a process in which a gaseous mixture containing substituents such as carbon oxides, nitrogen oxides, sulfur oxides, and oxygen is separated into two streams. One stream is desirably mixed with a ballast gas and sent into a reference arm of a measuring apparatus; a second stream is passed after mixing both with nitrogen and a carrier gas, such as helium, and subjected to an electric discharge. The thus treated gases are passed through a conventional electrometer. The excited $NO_x$ passes to an ionic state and gives off a measurable electron.

U.S Pat. No. 4,115,067 to Lyshkow suggests a process for using a substrate which is sensitive to the pollutant to be measured and monitoring the change in color or reflectivity of the sensitized substrate. Lyshkow suggests the use of a substrate upon which silica which has been impregnated with a mixture of sulfanilic acid and N-(1-naphthyl)-ethylenediamine dihydrochloride. The mixture reacts with $NO_2$, changes the color of the substrate, and decreases the reflectivity of the substrate having the silica gel coating. Lyshkow suggests that the treated substrate be contacted with the gas to be measured and moved at a constant rate past a device which measures the change of reflectivity of the surface. In this way the amount of $NO_2$ is measured.

The U.S. Pat. No. 4,778,764 to Fine describes a device and a process in which a sample is injected with a solvent into a chromatographic column to separate the various materials present in the sample. The output of the column is then burned in the presence of a variety of detectors for one or more of $NO_x$, $SO_2$, $CO_2$, and halogens.

U.S. Pat. No. 4,840,913 to Logothetis et al. suggests a method for sensing nitrogen oxides, particularly in the exhaust flow of an internal combustion engine. The gas is passed through an oxidation catalyst which is formed over an oxide sensor. The oxidation catalyst is intended to oxidize all reducing species (CO, $H_2$, hydrocarbons, alcohols, etc.) which are carried in the gas to be measured. Nitrogen monoxide is oxidized to $NO_2$ as well. The oxidized gas passes to an oxide sensor such as a $SnO_2$ or ZnO.

U.S. Pat. No. 4,473,536 to Carberg et al. suggests a process for controlling a $NO_x$ reduction process using a $NO_x$ sensor.

None of the above disclosures suggest a process or an apparatus in which a catalytic sensor element is used to detect the presence of a gaseous component.

The concept of using the temperature rise of a gas as it passes through a catalyst bed as an indicator of the content of a component of that gaseous mixture has been shown. For instance, in U.S. Pat. No. 2,751,281 to Cohen, a method is taught for measuring low concentrations of gas impurities (such as oxygen) in the range of 0.0001% to 0.001%. A thermocouple is placed such that a cold reference junction is on the upstream side of a bed of catalyst and the hot junction is placed on the downstream side of that bed. As the gas flows across the catalyst, the temperature of the gas rises, is detected, and the content of the incoming gas calculated. U.S. Pat. No. 3,488,155 to Ayers shows a similar process in which the temperature on each side of a hydrogenation catalyst bed is measured during the flow of a gas containing hydrogen. The temperature difference is related to the hydrogen content of the incoming gas stream.

The U.S. Pat. No. 3,537,823 to Ines suggests a process for measuring the quantity of "smog forming hydrocarbons in a gas sample" by measuring the temperature rise in an oxidation catalyst bed. Moreover, a related process is found in U.S. Pat. No. 3,547,587 also to Ines.

U.S. Pat. No. 3,607,084 to Mackey et al. teaches a process for the measurement of a combustible gas content by locating a pair of wires in a small chamber containing a volume of gas with combustibles therein. One wire is coated with a catalytic mixture of a metal oxide and a powdered metal of the platinum group and the other is apparently uncoated. Electrical power supplies heat to both wires. The difference in resistance caused by the change in temperature of the wire coated with the catalytic mixture provides an indicator of the amount of combustibles in that gas chamber.

U.S. Pat. No. 4,170,455 to Henrie also suggests a method for the monitoring of the hydrogen or oxygen content of a gas stream by measuring the temperature upstream and downstream of an oxidation catalyst.

U.S. Pat. No. 4,343,768 to Kimura shows a gas detector formed using semiconductor technology. The detector uses dual heating elements over a channel adapted for gas flow. One of the heating elements is coated with a "catalytic or gas responsive film" which may be platinum or palladium. The increase in the temperature of the catalytic film is detected in terms of the variation in electrical resistance in the content of the gas stream calculated.

Finally, U.S. Pat. No. 4,355,056 to Dalla Betta et al. suggests a differential thermocouple combustible sensor in which one junction of the thermocouple is catalytically coated and the other junction is not. The gas stream contains such gases as carbon monoxide and hydrogen and is said to be "insensitive to contaminants such as $SO_2$ and NO".

None of these disclosures teaches the necessity for satisfying the dimensionless criteria specified here nor are any of the processes disclosed sensitive to the presence of $NO_x$, particularly when used with a reductant such as those disclosed here.

This invention is a sensor assembly having a functionally specific configuration of a catalytic element having an integral thermally isolate temperature measuring device, e.g., a thermistor or RTD (Resistance Temperature Device). Another portion of the sensor may be a temperature reference element.

This sensor configuration, particularly in conjunction with the inventive process, permits fast resolution of the $NO_x$ content of the gas passing by the sensor to a high degree of accuracy and is insensitive to interference from other gas components in the measured stream.

SUMMARY OF THE INVENTION

As was noted above, the invention is a sensitive $NO_x$ sensor and a process for using the sensor to measure $NO_x$ in a flowing gas stream.

The sensor assembly itself may be made up of two major discrete functional portions: a catalytic sensor element and a reference sensor element. The catalytic element has on its outside periphery a catalyst; in thermal contact is a temperature measuring device. Both are generally thermally isolated from the operating environment and each other. The catalyst is selected and merged with the temperature measuring device so that the $NO_x$ in the gas stream is selectively reduced to $N_2$ on the catalyst surface using an added reducing gas. The temperature measuring device may be a device such as an RTD, a thermistor, or a thermocouple which detects the small temperature rise which occurs due to the $NO_x$ reduction reaction taking place on the catalyst. The catalyst and temperature measuring device should be in close (ideally, contiguous) physical proximity and constructed in such a way that they retain most of the heat of reaction produced by the reduction reaction. The heat of reaction should then cause only the temperature of the temperature measuring device in communication with the catalyst to rise. Baffles or shields may be used in the vicinity of the catalytic sensor element to lessen the amount of heat which is radiated away from that catalytic element either to the reference element (if one is used) or to other surrounding portions of a sensor instrument.

The sensor assembly may be configured so that the gas flows past the catalytic and reference elements at temperatures, flow rates, and reductant concentrations which meet the dimensionless criteria (the various Damkohler Numbers) discussed below.

The measuring process used in conjunction with this device is one in which a reductant such as $NH_3$, cyanuric acid, urea, ammonium carbonate, ammonium carbamate, ethyl carbamate, gaseous amines, or other similar $NO_x$ reductant is introduced into the $NO_x$-containing gas upstream of the sensor assembly. The reductant is introduced in an amount large enough to assure that all of the $NO_x$ present is reduced on the catalyst surface.

The mixture of reductant and $NO_x$-containing gas is then passed over the catalytic and reference sensor elements. The temperature and flow rate of the mixture are conditioned so that the certain dimensionless criteria describing the chemical reaction rate, molecular diffusion rate, and reactant bulk transport rate are satisfied, i.e.:

I. The Second Damkohler Number ($Da_{II}$) for the $NO_x$ in the $NO_x$ reduction reaction should be much greater than 1, II. $Da_{II}$ for the reductant in the $NO_x$ reduction reaction should be much less than 1, III. $Da_{II}$ for the reductant in the reductant oxidation reaction should be less than 1, and IV. The First Damkohler Number ($Da_I$) for the $NO_x$ in the $NO_x$ reduction reaction should be less than or equal to 1.

The temperature of the catalytic sensor element is obviously converted to an electrically measurable quantity (voltage, resistance, etc.) by the temperature measuring device and is compared to the analogous quantity from the reference element. The difference in temperature is proportional to the $NO_x$ concentration in the measured gas. Calibration of the sensor element assembly, as with all good instrumentation, is both desireable and necessary.

DESCRIPTION OF THE INVENTION

The invention is both a $NO_x$ sensor capable of measuring low $NO_x$ concentrations and a process for detecting and measuring $NO_x$ in a flowing gas stream using that sensor.

$NO_x$ Sensor Assembly

The inventive sensor assembly is made up of two major components which are critical to its operation (the catalytic sensor element and the reference element) and a number of other components which in some configurations may lend ease of operation and reliability to its use.

First, the catalytic sensor element is made up of a catalyst and a temperature measuring device.

Figure 1:
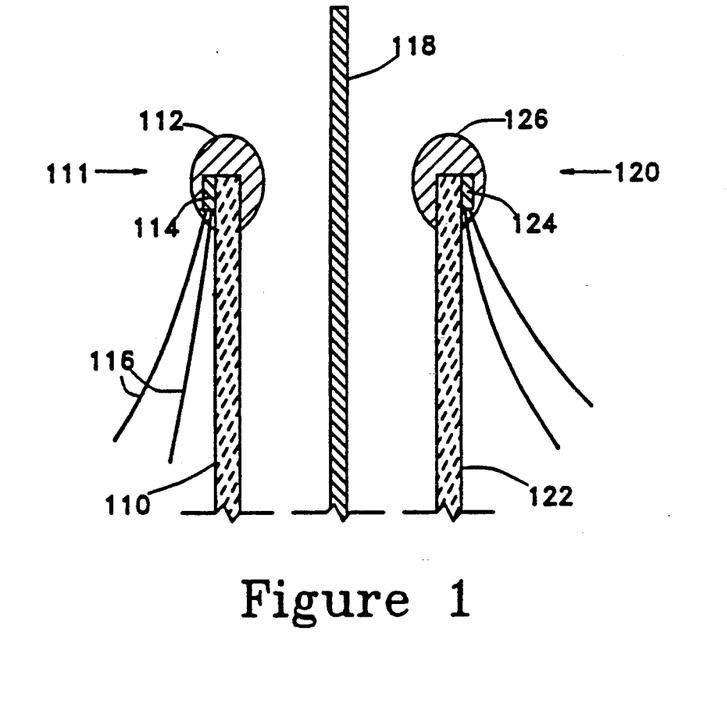
FIG. 1 depicts typical sensor element set useful in the inventive sensor device.

FIG. 1 shows a cutaway schematic depiction of a catalytic sensor element (111) and a reference element (120) within the scope of the invention. This variation of the inventive device uses a thermally insulating support or substrate (110 and 122) as a portion of the element. These supports allow the respective elements to be used as probes or fingers extending into a flowing gas stream. The substrate should be a thermally insulating support having sufficient mechanical strength to support the catalyst and temperature measuring devices in the flowing stream. The substrate (110) may be any material suitable for supporting the temperature measuring devices discussed below, but desirably is a ceramic or a ceramic coating on a metallic support. Suitable ceramic materials include fired kaolin, alumina, silica-alumina, and silica. Ceramic materials which are typically used as catalyst supports are also suitable for the substrate providing that they possess the necessary mechanical strength to withstand the temperature cycling steps as the device is turned on and off, the lengthy times the element will spend at the desired operating temperature, and the normal mechanical shocks endured during installation and operation. These ceramic materials are also suitable because of the variety of procedures available for making the catalytic material (112) adhere to the ceramic substrate (110).

The temperature measuring device (114) may be any of a variety of devices which produce a variation in a measurable physical quantity, e.g., voltage or resistance, as the temperature of the device changes. A bimetallic thermocouple, particularly a chromel-alumel thermocouple, may be cemented to the substrate (110) using known and available ceramic cements. The sensitivity of the chosen temperature measuring device must match the sensitivity of the resulting analyzer. For instance, as a rule of thumb, thermocouples may be accurate only to a ±1F°. In measuring low levels of $NO_x$, such as levels below 60 ppm, a more sensitive temperature measuring device may be necessary. The face of the temperature measuring device away from the support should be substantially free of gas barriers so that the gas to be measured contacts the catalytic surface (112). The temperature measuring device may be a thermistor chosen for appropriate sensitivity in the proper temperature range. If a ceramic substrate (110) is selected, the temperature measuring device need not be discrete and assembled onto the substrate but may instead be made directly on the ceramic surface by known technologies. See, for instance, the procedure for creating thermistors on a ceramic substrate shown in U.S. Pat. No. 4,129,848 to Franc et al. The leads (116) from the temperature measuring device would allow the variable physical quantity corresponding to temperatures of the device to be measured. The temperature measuring devices may be placed within the substrate; the substrate may be formed from a thermowell.

Finally, the catalyst layer (112) may be fairly thin to promote conduction of the heat of reaction produced at the surface to the temperature measuring device (114) and to reduce the thermal mass of the catalyst sensor element. There are a number of suitable catalysts for the following reactions illustrated using ammonia as the reductant:

$$4 NO + 4 NH_3 + O_2 \rightarrow 6 H_2O + 4 N_2 \tag{1}$$

$$6 NO_2 + 8 NH_3 \rightarrow 12 H_2O + 7 N_2 \tag{2}$$

Preferred catalysts include Group V and VIII transition metal catalysts such as iron oxides, cobalt oxides, and vanadium oxides.

The catalysts suitable for $NO_x$ reduction will likely also promote the oxidation of the reductant, particularly if the reductant is ammonia, to $NO_x$ at higher temperatures via the following reaction:

$$4 NH_3 + 5 O_2 \rightarrow 4 NO + 6 H_2O \tag{3}$$

Because of the desirability of producing a catalyst layer of minimal thickness, the catalyst or catalyst precursor may be applied using a liquid having little or no solids content. For instance, a catalyst precursor of a dissolved or chelated catalytic metal, e.g., an acetylacetonate, in a suitable solvent, e.g., dimethyl formamide, may be used to impregnate the ceramic surface. Once dipped, sprayed as a wash coat, or otherwise impregnated, the element may be calcined in oxygen or air to produce an active catalyst. Reduced platinum group metals such as platinum or palladium, although suitable, may be less desireable at certain higher operating temperature ranges because of their proclivity for oxidizing residual combustion products such as CO, $H_2$, or hydrocarbons.

A particularly suitable procedure for applying the catalyst to the catalytic sensor element is via use of metal salts of the appropriate catalytic metal to the element support. The salt, preferably a sulfate or chloride, is applied as a saturated aqueous solution to maximize the available catalytic metal to the element.

In some applications a baffle or shield (118) is desired to minimize radiant and convective heat loss from the catalytic surface (112) to the reference element or other cooler portion of the sensor assembly.

Second, the reference element (120) may be similar in design to the catalytic element (111) except that the catalyst layer is excluded and an optional protective layer (126) for the temperature measuring device may be added.

The reference element (120) is intended to provide a comparative temperature measurement which temperature is that of the non-reacted gas flowing past the reference element or catalyst sensor element. The reference element may, in fact, be an arbitrarily selected fixed value element if the temperature of the gas and the environment "seen" by the catalytic sensor element can be carefully controlled. For instance, if the catalytic sensor element is placed in an iso-thermal environment such that the surrounding temperature is controlled rather than measured, a precision resistor (if the temperature measuring device for the catalytic sensor element is an RTD or a thermistor) or a voltage source (if the temperature measuring device is a thermocouple) may be used instead of a reference element which measures local temperature.

Neither element is directly heated using current flowing through the sensing element, e.g., resistance heating.

In FIG. 1 the reference element (120) is made up of a mechanical support, a temperature measuring device, and an optional protection layer. The variation shown in FIG. 1 includes a mechanical support (122) similar in function support (110). The temperature measuring device (124) is mounted on the support or, as with the catalytic element, may be produced integrally with the ceramic surface of the support if, of course, the support is ceramic. The protective coating (126) is optional depending upon the corrosivity of the gas stream measured and the reactivity of the temperature measuring device employed.

The optional protective coating (126) on the reference element (120) may be of alumina, silica, epoxide resins, carbon, or other heat conducting material. The coating is to protect the temperature measuring device (124) from corrosive elements, e.g., $SO_2$, $SO_3$, $NO_2$, $H_2O$, etc., in the gas stream but should not interfere in the reference element's task of measuring local temperature. Additionally, the protective coating (126) improves the match of the thermal mass of the reference element (120) and the catalytic sensor element (111). If the catalytic sensor element (111) were to be coated with a catalyst and the reference element were not, the thermal mass of the reference element would be much less and would respond to changes in ambient flowing gas temperature much more quickly than the catalytic sensor element. Such a response difference clearly could cause errors in the $NO_x$ measurements. Further, the protective coating (126) provides cross-sectional and surface areas of the reference element (120) relatively similar to those of the catalytic sensor element (120). Similarity in those areas results in similar convective heat transfer loads.

Desirably, to equalize the thermal emissivity of the two elements, the color of the protective coating (126) may be matched to the color of the catalytic sensor element (111) and the surroundings. Although, the heat loss by this route is minimal, the effect can be minimized.

The reference element (120) desirably is designed so that the configuration of the gas as it flows past is similar to the flow past the catalytic sensor element (111). Said another way, the aerodynamic shapes of the two elements should be similar. The two elements ideally should be placed in similar and representative flow regions in the measured gas, i.e., both may be placed in a turbulent flow region of the gas so that the gas measured is equally representative. For instance, placement of one element in a laminar flow region and another in a turbulent flow region should be avoided in that it causes unequal measurements of the gas stream's incoming temperature.

The two elements should be optimized in shape and materials of construction to minimize heat loss via conduction or radiation. Support materials should be selected so that the heat of reaction on the catalytic coating (112) of the catalyst sensor element (111) is maintained at the temperature measuring device (114). The elements should be as small as is practically possible so to permit rapid response to temperature and $NO_x$ content. Use of small elements also results generally in less radiation heat loss to the surroundings. The two elements should have similar thermal mass and should, as much as is possible, be light colored (preferably white) to minimize radiation or, at the very least, be the same color. The catalytic sensor and reference elements need not be in the configuration shown in FIG. 1. Other suitable variations are schematically shown in FIGS. 2 through 4.

Figure 2:
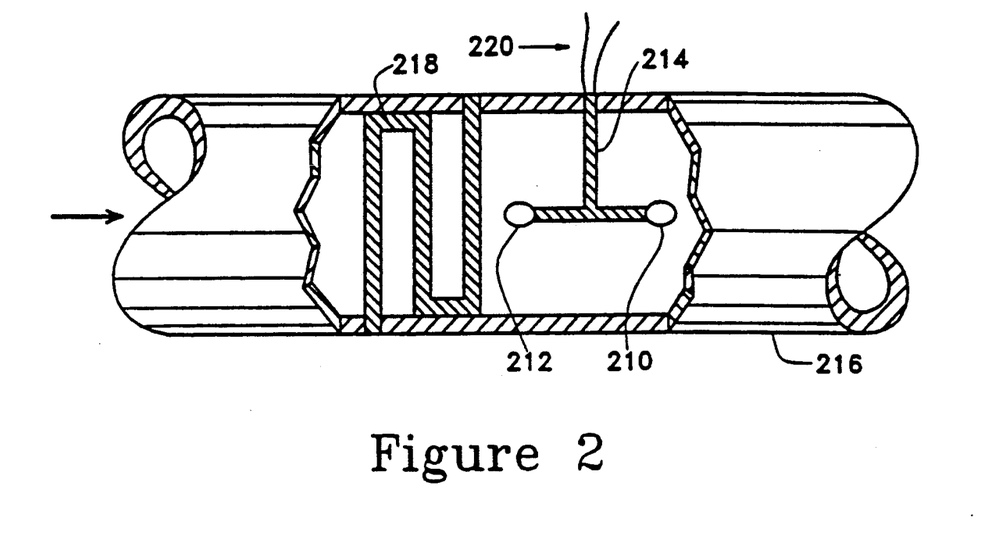
FIGS. 2, 3, and 4 are other variations of the sensor elements in the inventive sensor.

The configuration shown in FIG. 2 supports both the catalytic sensor element (210) and the reference element (212) on a T-shaped thermally insulating support (214). The reference element (212) should be placed upstream so that it does not detect any substantial amount of heat which may be produced on the catalyst surface of catalytic sensor element (210). The support (214) is fixed so that the elements are in an appropriate flow region of the sample line (216). A gas preheater (218) is shown schematically in FIG. 2. As is discussed below in greater detail, the operating temperature of the catalytic sensor element is to be controlled so that the dimensionless criteria discussed there are satisfied. The details of the two elements are similar to those in the elements of FIG. 1, e.g., the catalytic sensor element has an outer catalytic layer suitable for reducing $NO_x$ to $N_2$ using certain reductants and an inner temperature measuring device. The reference element (212) also is made up of a temperature measuring device optimally covered by a protective layer. Signal leads (220) from the temperature measuring devices found in the elements are also shown.

Figure 3:
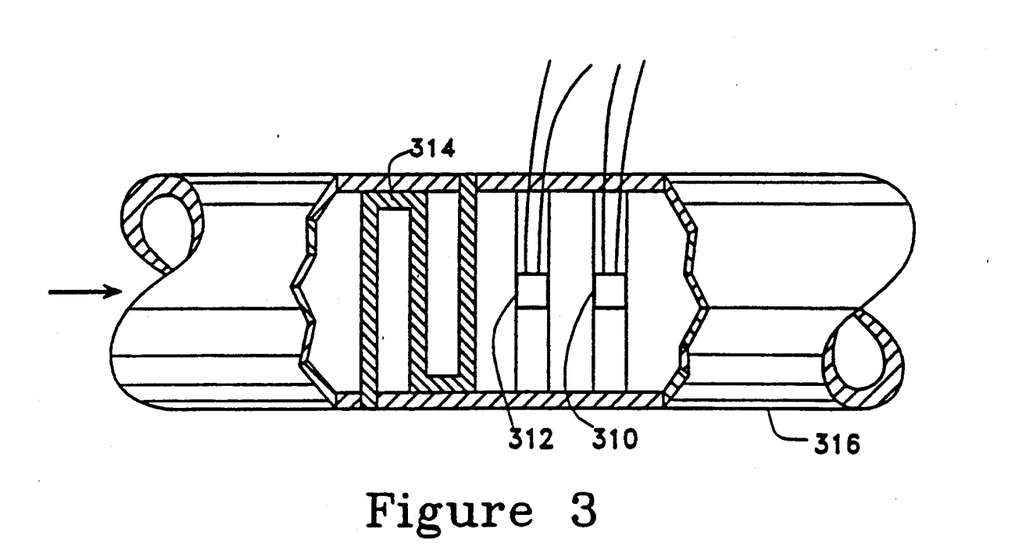

The schematic variations shown in FIG. 3 use members traversing a flow channel to support the catalytic sensor and reference elements. As with the other variations, the catalytic sensor element (310) is downstream of the reference element (312) and, in turn, is downstream of a sample gas preheater (314). This configuration also desirably places the elements in the portions of the sample line (316) having the greatest chance for thorough mixing.

Figure 4:
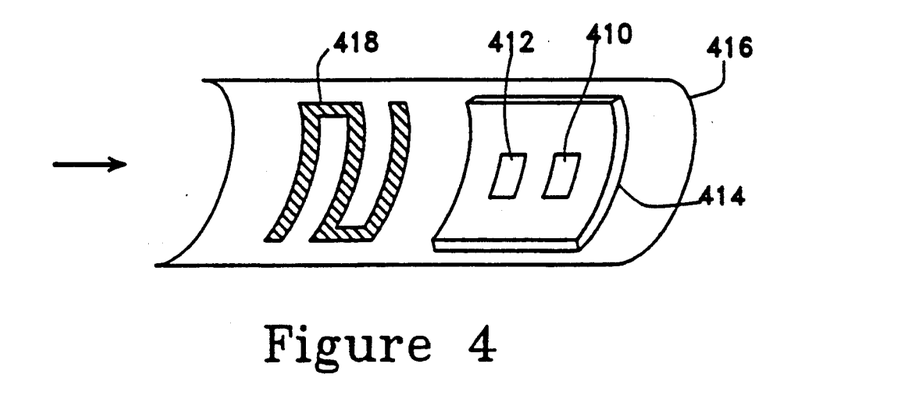

FIG. 4 shows another variation of the inventive device in which the elements are mounted in the wall of the sample line. Catalytic sensor element (410) is downstream of the reference element (412). The two elements are mounted in an insulating support (414) which may be mounted on the inside surface of a sample line (416) or as a cutaway window in the wall of the sample line (not shown). The gas preheater (418) is upstream of the elements. This configuration is less desireable (but is operable) in that flow disruptors may be desirable to create disturbances in the wall boundary layer and to assure good mixing of the $NO_x$ reductant with the gas to be measured.

The variations of catalytic sensor elements and reference elements shown in FIGS. 1 through 4 are best employed in a sensor assembly in which the flow rate of the gas being measured and its temperature are controlled to meet the dimensionless criteria specified below. The sensor assembly may also include a source of $NO_x$ reductant and an appropriate device for thoroughly mixing the reductant with the measured gas before that mixed gas passes the element set.

The signals emanating from each of the temperature measuring devices in the catalyst element and the reference element are compared using well-known circuitry (wheatstone bridges, differential amplifiers, etc.) and the $NO_x$ content of the gas stream measured via calibration. Because of the linearity of the inventive assembly, the $NO_x$ concentration may be measured directly after such calibration.

The exceptional sensitivity of this sensor assembly is achieved by carefully controlling a number of operating and assembly design parameters which are discussed below.

As was mentioned above, there are a number of catalysts suitable for selectively reducing $NO_x$ to $N_2$ and $H_2O$ using this invention. The activity and selectivity of these catalysts obviously will vary from one to the other. However, by selecting flow rates and operating temperatures suited to the selected catalyst, the effect of the catalyst choice on device sensitivity can be minimized.

Two independent rates determine the actual rate of reaction for $NO_x$ reduction on the catalytic element surface as follows:

1. the localized rate of $NO_x$ reduction at the catalyst surface and
2. the rates at which $NO_x$, $O_2$, and the reductant diffuse to the catalyst surface.

The slower of these two processes typically controls the overall reaction rate. The overall reaction rate in the device of this invention is measured as a temperature rise at the catalyst element. However, either the diffusion rate or the reaction rate may be slower and thus curtail the overall reaction rate. For this application it is desireable that the mass transfer or diffusion rate of $NO_x$ to the catalyst surface be the slower of the two rates. In this way the response from the sensor is generally linear with respect to the $NO_x$ concentration in the measured gas stream.

This result is achievable by selecting a temperature, $O_2$ concentration, and reductant concentration such that the ratio of rate of reaction for the $NO_x$ to the $NO_x$ diffusion flux is very much greater than 1. This ratio (for $NO_x$ reduction according to Reaction No. 1 above) may be expressed in dimensionless terms as its Second Damkohler Number:

$$Da\int_{II(1)}^{NO_x} = \frac{\text{Chemical Reaction Rate}}{\text{Molecular Diffusion Rate}} >> 1$$

The intrinsic reaction rate for $NO_x$ is not a simple expression in that (for the species NO):

$$r = ke^{-R/T}p_{NO}^n p_{O_2}^m p_{NH_3}^j.$$

A wide range of linear and nonlinear reaction rates has been reported for this reaction in the literature with corresponding values of n=0.2 to 1.0, m=0.12 to 1.0, and j=0 to 0.25. A discussion of Damkohler Numbers and other such dimensionless numbers may be found in Catchpole et al., "Dimensionless Groups", I & EC, Vol. 58, No. 3, pp. 46–60 (March, 1960). Because of the complexity of computing this ratio directly, an experimental procedure was devised to determine the point where the $$Da_{II(2)}^{NO_x} \text{ and } Da_{II(1)}^{NO_x}$$

is greater than 1. For a fixed flow rate of $NO_4$-containing gas, $O_2$ concentration, reductant concentration, and $NO_x$ concentration, the temperature of the mixed gas and the probe assembly is continually increased and the catalyst element output measured. The output increases until a plateau is achieved. Once the temperature reaches a level where reaction rate at the catalyst surface is significantly faster than the $NO_x$ diffusion rate to the surface, the temperature dependence of $Da_{II(3)}$ becomes minimal. The sensor output signal becomes essentially flat in the desired gas temperature operating range as shown in FIG. 5.

A family of these temperature/output graphs may be determined for the $NO_x$ range which will be encountered in operation. The operating ranges for several $NO_x$ concentrations are shown graphically in FIG. 5. A temperature common to each of the operating ranges is selected ($T_{op}$). The temperature of incoming gas (containing reductant) is then adjusted so that it is at or near $T_{op}$ as it reaches the element set.

Figure 5:
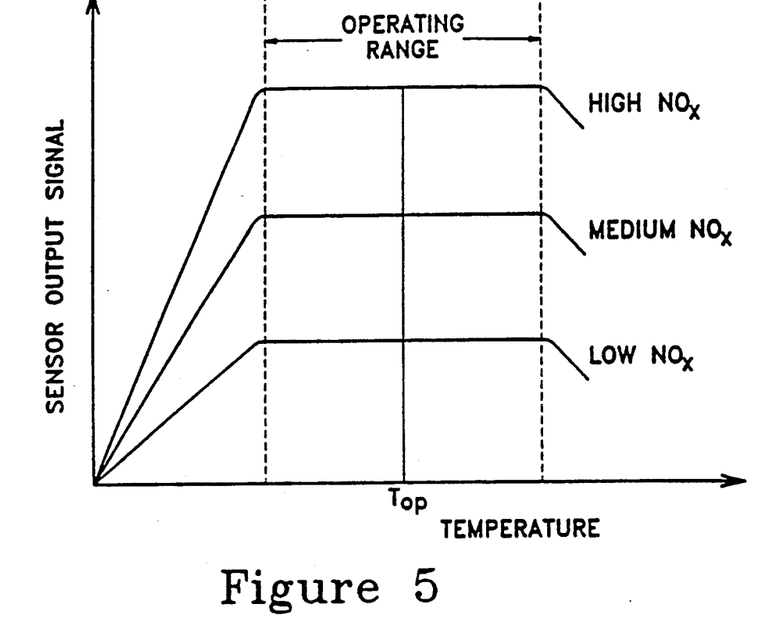
FIG. 5 is a graph of catalytic sensor output as a function of temperature and $NO_x$ input when the dimensionless reaction rate, flow rate, and diffusion rate criteria are satisfied.

It is clear that if the device were to be operated at a temperature below the operating range as shown in FIG. 5, the sensor response to a change in $NO_x$ concentration would not be linear, would be dependent on temperature, and would be dependent on any variable that affected the kinetic rate of $NO_x$ reduction, e.g., $O_2$ concentration, as shown in equation 4. The accuracy of the sensor would be reduced.

The Second Damkohler Number for the reductant in the $NO_x$ reduction reaction (Reaction No. 1 or 2 above) must be less than 1:

$$Da_{II(1 \text{ or } 2)}^{Red} = \frac{\text{Reductant Reaction Rate}}{\text{Reductant Molecular Diffusion Rate}} < 1$$

Conceptually, this means that the bulk transport rate (and resulting concentration) of the reductant to the catalyst surface must be sufficient so that it is larger than the removal rate of the reductant by reaction. This rate is adjusted by temperature, reductant concentration, and mixing.

The second Damkohler Number for the reductant in the reductant oxidation reaction, e.g., Reaction No. 3 above, must be much less than 1:

$$Da^{Red}_{II(3)} = \frac{\text{Reductant Reaction Rate}}{\text{Molecular Diffusion Rate}} << 1$$

The rate of oxidation of the reductant to, for instance, $NO_2$ must be quite low. This function is controlled largely by temperature. Certain operating regions where:

$$Da^{NOx}_{II(1\ or\ 2)} >> 1$$

have been found to overlap (to some extent) with operating regions where:

$$Da^{Red}_{II(3)} << 1$$

Another dimensionless operational parameter which must be satisfied for repeatable and accurate low level $NO_x$ detection is the First Damkohler Number ($Da_I$) which deals with gross mass transport of the reactant to the vicinity of the sensor element set. The First Damkohler Number is the ratio of disappearance of $NO_x$ (according to chemical equation 1 or 2 above) at the catalytic sensor element surface to the bulk transport rate of $NO_x$ to the element set:

$$Da^{NOx}_{I(1\ or\ 2)} = \frac{NO_x \text{ Reaction Rate}}{\text{Bulk Trasnport of } NO_x} \leq 1$$

This dimensionless number must be less than or equal to 1 but preferably much less than 1. Said another way: the bulk flow of gas containing $NO_x$ must be sufficient to give a representative sample from the gas stream measured, must be larger than the $NO_x$ diffusion rate controlling step to the surface, and must supply more $NO_x$ to the element set vicinity than the reaction at the catalytic element removes by reduction to $N_2$.

Figure 6:
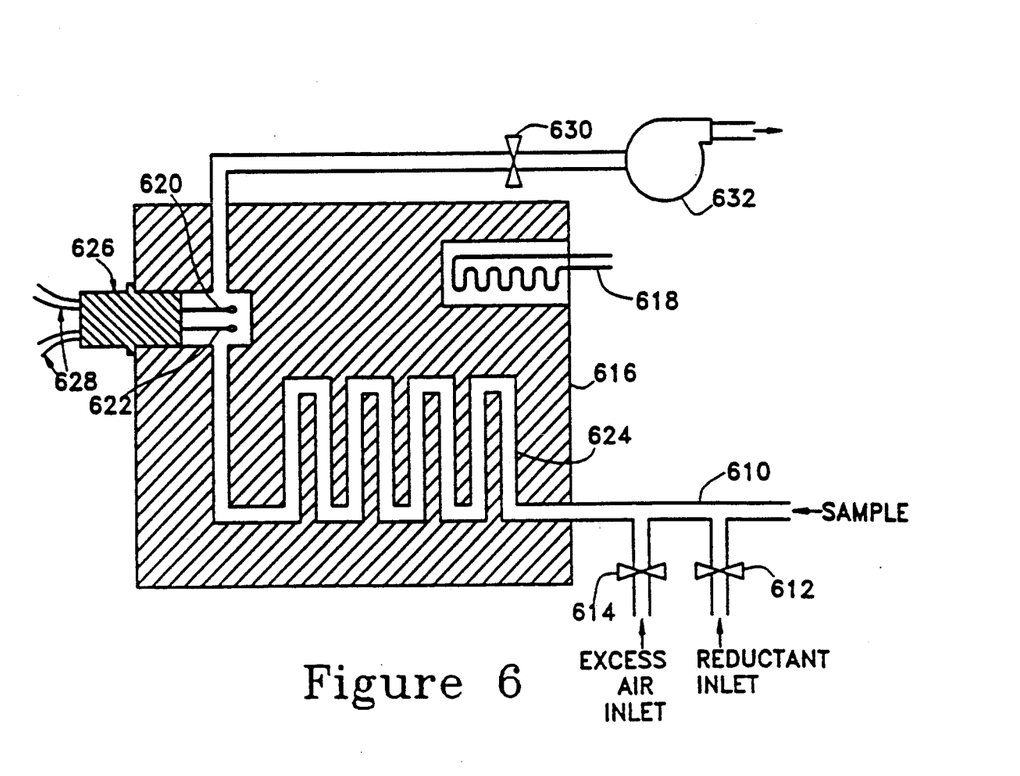
FIG. 6 is a cutaway depiction of a sensor assembly using one variation of the inventive sensor elements set.

These criteria may be satisfied through use of the sensor assembly shown in FIG. 6.

The gas to be sampled is drawn in through sample port (610) from the combustion gas stack which disposes of that combustion gas. A gaseous reductant, preferably $NH_3$ because of its ease of handling and selectivity towards reduction of $NO_x$, is introduced into the sample gas line by the reductant metering valve (612). excess of reductant over that necessary to react all $NO_x$ present in the sample gas is desireable. Valve (612) can be controlled in a closed-loop system based upon the content of $NH_3$ in the stream leaving this sensor assembly or may be simply fixed.

Excess $O_2$ may be introduced into the sample gas line by air control or metering valve (614). Additional excess air is not always a necessity in that the sample gas may contain sufficient oxygen to meet the requirements of the reduction reaction specified above. The mixture of sample gas, reductant, and excess air (if needed) then passes into a temperature controlled heat exchanger block (616) which has several functions but mostly provides an isothermal heat source which brings the sample gas mixture up to the operating range ($T_{op}$) discussed above. The block may contain one or more heater elements (618). A variation would be a heater external to the block which maintains the block at the desired temperature. In any event, the sample gas mixture passes through the heat exchange surfaces which may be in the labyrinthine form (624) shown in FIG. 6. After heating to the operating temperature, i.e., the temperature where $$Da^{NOx}_{II(1\ or\ 2)} >> 1$$

at the catalytic sensor element (620), the gas passes to the element assembly (626) of the form discussed above with regard to FIG. 1. The element assembly contains both a catalytic sensor element (620) and a reference element (622). The signal leads (628) from the temperature measuring devices in the element assembly are available for electronic processing to produce a signal indicative of the $NO_x$ content. The thus measured gas flow then exits the block (616). The flow rate of the sampled gas through the temperature controlled heat exchanger block (616) may be controlled by control valve (630) and vacuum pump (632). The control valve (630) may be another suitable flow control device, e.g., orifice, etc., which permits the Damkohler Numbers $Da_{I(1)}^{(for\ all\ reactants)}$ at the catalytic sensor element (620) to be less than or equal to 1. The pump (632) may be another suitable suction device such as an eductor, aspirator, or thermal siphon.

The sample gas may then be disposed of.

Nonessential portions of the $NO_x$ sensor which would nonetheless be apparent to an ordinary worker in this art have been omitted for clarity of discussion. For instance, the line supplying sample gas to the sensor apparatus should be maintained above the dew point to prevent problems with condensation and consequent loss of device accuracy. Similarly, a filter may be installed to remove particulates before the gas reaches the sensor element assembly.

$NO_x$ Detection Process

The process follows use of the $NO_x$ detector discussed above very closely.

A sample gas stream containing $NO_x$ is mixed with a $NO_x$ reductant which preferentially reduces $NO_x$ on the catalyst (discussed elsewhere herein) in the presence of $O_2$. This reductant typically contains a nitrogen/hydrogen bond. The reductant may be selected from the group of $NH_3$, cyanuric acid, urea, ammonium carbamate, ammonium carbonate, ethyl carbamate, and gaseous amines, etc. An excess of $O_2$ must be present in the gas stream before and after it passes the sensor element set.

The temperature of the mixture of reductant $O_2$ and sample gas containing $NO_x$ is then controlled by heating or cooling to the operating temperature. The operating temperature is a temperature such that $$Da^{NOx}_{II(2)}$$

for $NO_x$ is much greater than 1 at the catalyst sensor element.

The heated mixture is passed over the catalytic sensor element comprising a temperature measuring device and a catalyst. The catalytic material may be selected from those discussed above. The catalyst will cause the reductant to exothermally reduce the $NO_x$ to $N_2$ and $H_2O$ and raise the temperature of the catalytic element. The reactant $NH_3$ is not substantially oxidized at the operating temperature. The increased temperature will be measured by the temperature sensing device producing a measurable output approximately proportional to the rise in temperature. The temperature sensing device may be a thermocouple suitable for the necessary sensitivity and temperature range. If a thermocouple is used in the temperature sensing device, the output from the device will be a voltage. If other devices are used, e.g., RTD or thermistors, the resistance of the device will vary with the temperature. An appropriate voltage would then be applied to the temperature measuring device and the resulting resistance detected. Temperature measuring devices based on optical operating principles are also known. One suitable optical temperature measuring device is found in U.S. Pat. No. 4,861,979.

The mixed gas may also be passed over a reference element which comprises a temperature sensing device of the same type found in the catalytic sensor element. The temperature sensing device provides an output which is then compared to the output from the catalytic element and the difference in the element outputs determined. The $NO_x$ content is calculated from this difference in output between the elements.

The flow of mixed gas across the two catalytic sensor elements is such that $$Da_{I(1 \text{ or } 2)}^{NO_x}$$

is less than or equal to 1.

EXAMPLES

The sensor and process have been described in detail above. The following examples show various aspects of the invention but are not to be considered as limiting the scope of the invention's disclosure.

EXAMPLE 1

This example shows the preparation of an element set suitable for use in this invention.

An opposed thermocouple sensor similar to that shown in U.S. Pat. No. 4,355,056 was selected as the element set. Each element was made up of an alumina bead and a thermocouple. The catalyst element was made by impregnating the alumina bead with a solution of 0.20 g of vanadyl acetylacetonate dissolved in 1.0 g of dimethyl formamide. The impregnation was carried out by dipping the alumina-bearing element in the solution and withdrawing and removing excess solution from the bead by blotting. The element was then dried at 125° C. The impregnation, blotting, and drying was repeated nine more times. Subsequently, the element was calcined in air at 500° C. A low surface area inert alumina coating was applied to the reference element using the process of U.S. Pat. No. 4,355,056. The reference element was then calcined at 500° C.

EXAMPLE 2

This example shows the preparation of another element set using an adjunct layer of titanium dioxide over the alumina support prior to addition of the catalytic metal.

A sensor assembly prepared as in Example 1 was prepared in the following manner. The catalytic element was treated with titanium isopropoxide to form a titanium dioxide layer over the alumina. More specifically, the alumina bead was dipped in a solution of 1.0 g of titanium isopropyloxide in 1.0 g of hexane and then calcined at 300° C. The operation of dipping in the titanium solution and calcining was repeated ten more times. During the final calcination, the sensor was heated to 500° C. Vanadium (as the catalytic metal) was impregnated into the titanium oxide/aluminum oxide bead using the method shown in Example 1, using six impregnations of a solution of 0.017 g vanadyl acetylacetonate in 1 g of acetonitrile, and finally calcined at 500° C. Low surface area alumina was added to the reference element also as described in Example 1.

EXAMPLE 3

This example shows the use of the element set of Example 2 in the device shown in FIG. 6.

Figure 7:
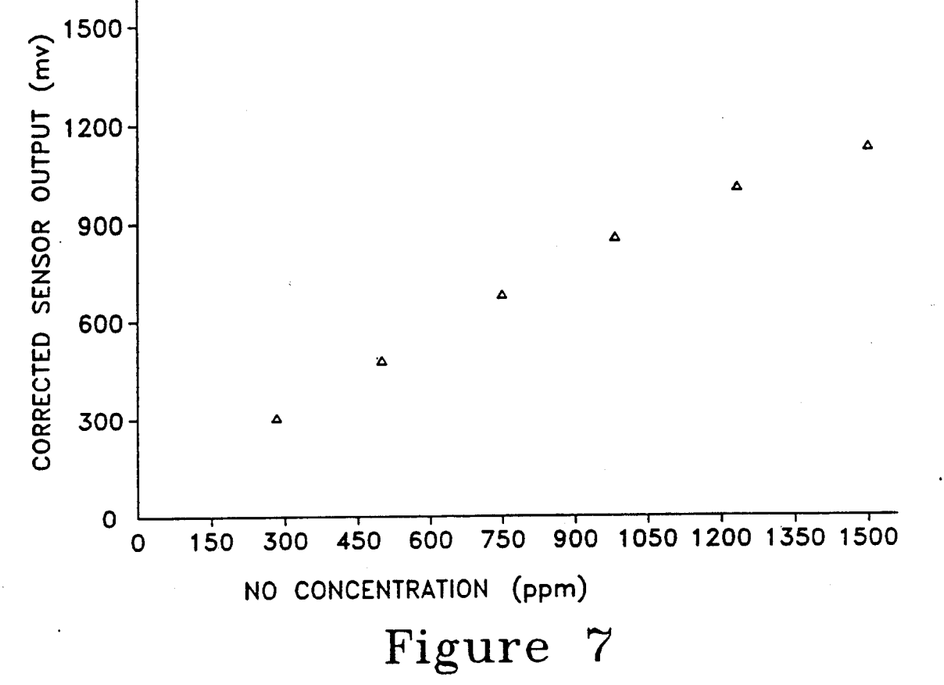
FIG. 7 is a graph of $NO_x$ concentration (0-1500 ppm) versus sensor output signal for one variation of the inventive sensor.

The temperature of the block was maintained at approximately 350° C. A gas stream containing 95% nitrogen, 5% oxygen, and 1200 ppm ammonia was then passed over the element set and the voltage output of the differential thermocouple element set monitored. As NO was added to the gas stream, a response in signal output directly proportional to the nitrogen oxide concentration was measured. The relationship is shown graphically in FIG. 7 as a plot of the output voltage in microvolts as related to the nitrogen oxide concentration in ppm.

EXAMPLE 4

The following example was done to demonstrate the relationship between $NO_x$ input, temperature, and catalytic sensor element output when all other variables are held constant.

The sensor in this example was produced using supports comprising a steel core coated with alumina and alundum layers. The temperature measuring devices were 100 ohm RTD's and were cemented to the coated substrate. The catalytic element and the reference element were then dipped in a saturated aqueous solution of $TiOSO_4$, blotted to remove excess solution, dried, and calcined in air at 500° C. after being progressively ramped to that temperature from ambient in about two hours. The catalytic element was then dipped in a saturated aqueous solution of $VOSO_4$, blotted to remove excess solution, and exposed to gaseous $NH_3$ for about 30 seconds. The catalytic sensor was now brown. They were dried at 125° C. for one hour. The catalytic sensor (now black) was heated in air at 500° C. after an initial two hour linear ramp-up at 4° C./minute from ambient temperature. A catalytic sensor element and a reference element were assembled into a set resembling (626) in FIG. 6.

The assembled sensor element set was introduced into an isothermal block having heaters and passageways to allow passage of the measured gas to the elements at sufficient flow rate (1000 sccm) and a variable temperature (225° C. to 325° C.). The concentration of NO was varied incrementally from 100 ppm to 1000 ppm. The $NH_3$ concentration in the gas stream was 1500 ppm and the $O_2$ concentration was abut 4.9%. For each concentration level of NO used, the temperature at the sensor element set was varied across the temperature range. At each noted temperature, the process was operated for 30 minutes to assume stable sensor output.

Figure 8:
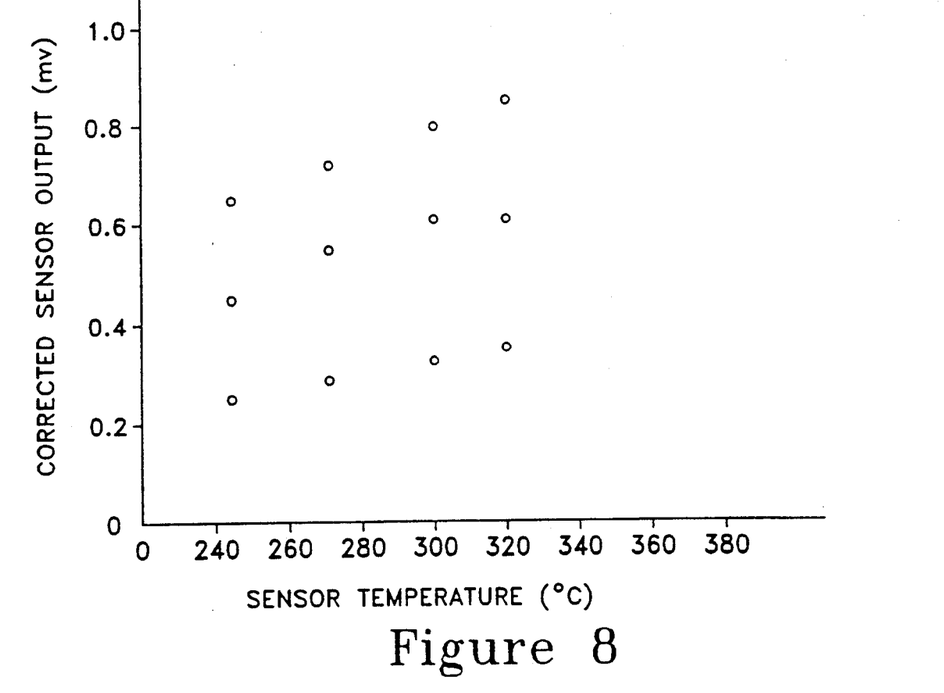
FIG. 8 shows a family of graphs comparing for various $NO_x$ concentrations the relationship of temperature versus sensor output signal.

As may be seen in FIG. 8, the output signal exhibited substantially flat behavior between 300° C. and 320° C.

The $T_{op}$ for this device would be below about 320° C.

EXAMPLE 5

This example shows the production and operation of a $NO_x$ sensor capable of accurately detecting low levels of $NO_x$. The operation is demonstrated in a typical exhaust stream containing variously NO alone, NO and $SO_2$, and NO and CO. This example demonstrates that the sensitivity of the inventive devices for $NO_x$ is not substantially affected by the presence of other pollutants.

The sensor elements used in this example were prepared using stainless steel bodies and thin, narrow element blocks of alumina (about 0.040"×0.250"). Temperature measuring devices (100 ohm RTD's) were cemented to the element blocks. The element blocks were mounted in the body using a ceramic cement so that about ⅜ inches was exposed. Both sensor elements were then coated with an alumina gel and calcined by heating the elements in an air furnace from room temperature to 500° C. and holding them at 500° C. for one hour. The elements were then dipped in a saturated solution of $TiOSO_4$. The elements were then dried in two stages: first at 80° C. and then at 475° C. for 1 hour.

The catalytic element was then dipped in a saturated solution of $VOSO_4$, dried, and calcined. This element set was inserted into an isothermal aluminum block similar to that shown in FIG. 6. The block and the incoming gas (1000 sccm) containing NO were preheated to 300° C. Reductant $NH_3$ in the amount of 1500 ppm was added to the gas stream. The $O_2$ concentration in the stream was 9.85%.

The NO was initially introduced at a level of 100 ppm and the process allowed to stabilize. A stabilized signal was usually achieved quickly; the measurement was usually taken at 12 to 15 minutes to assure a proper reading. The NO content was reduced in increments by 20 ppm or 10 ppm (i.e., to 80, 60, 40, 20, 10 ppm); measurements for 475 ppm CO and 500 ppm $SO_2$ were taken at each NO level. The output from the sensor elements at those data points are shown below:

TABLE

| Run # | NO (ppm) | $SO_2$ (ppm) | CO (ppm) | Corrected Output (mv) |
|---|---|---|---|---|
| A | 100 | — | — | 1.241 |
| B | 100 | 500 | — | 1.241 |
| C | 100 | — | 475 | 1.225 |
| D | 80 | — | — | 1.134 |
| E | 80 | 500 | — | 1.149 |
| F | 80 | — | 475 | 1.136 |
| G | 60 | — | — | 1.043 |
| H | 60 | 500 | — | 1.068 |
| I | 60 | — | 475 | 1.042 |
| J | 40 | — | — | 0.953 |
| K | 40 | 500 | — | 0.984 |
| L | 40 | — | 475 | 0.952 |
| M | 20 | — | — | 0.869 |
| N | 20 | 500 | — | 0.903 |
| O | 20 | — | 475 | 0.869 |
| P | 10 | — | — | 0.825 |
| Q | 10 | 500 | — | 0.856 |
| R | 10 | — | 475 | 0.829 |

Figure 9:
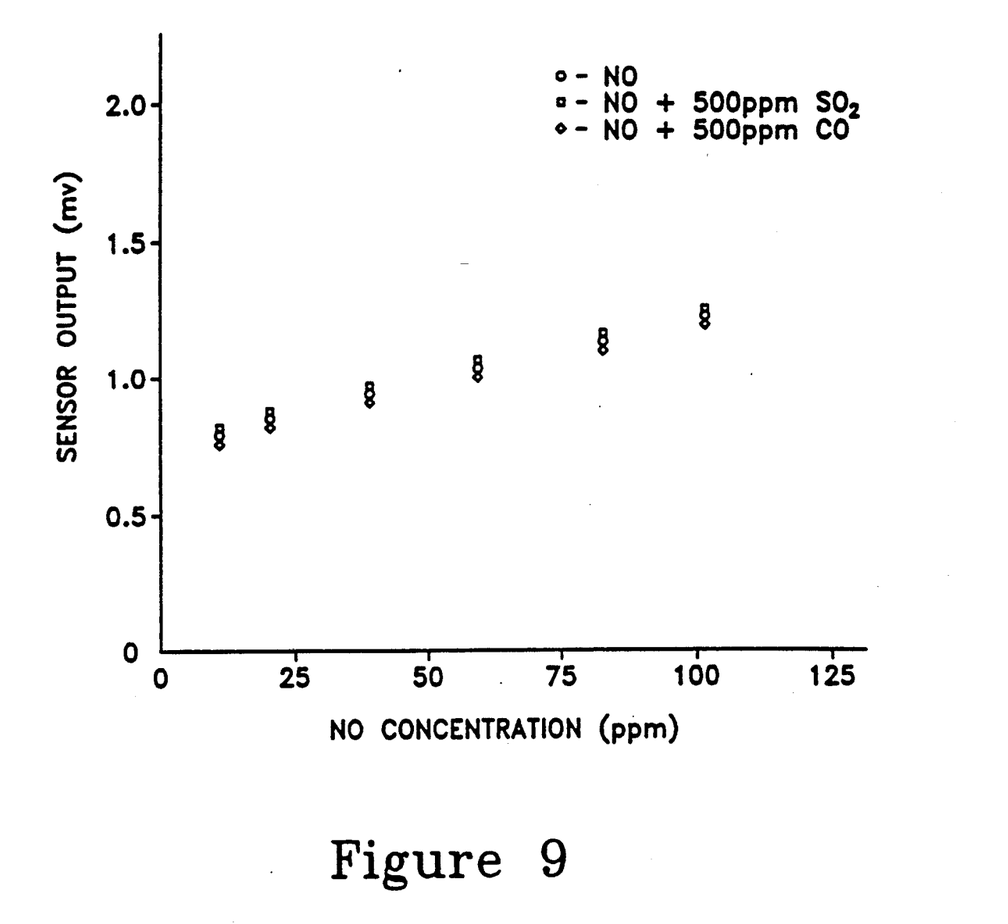
FIG. 9 shows the operation of one embodiment of the inventive sensor used on a low level $NO_x$ stream when the pollutants $SO_2$ and CO are present.

This information is shown in FIG. 9. As is shown there, the relationship between NO and output from the two sensor elements is linear throughout the range. Neither the presence of $SO_2$ nor that of CO had any more than a minor effect on the electrical output from the sensor elements. Clearly the sensors measure low concentrations of NO with good accuracy and the presence of other pollutants does not substantially affect that accuracy.

EXAMPLE 6

This example shows the production and operation of a $NO_x$ sensor using iron as the catalytic material on the catalytic sensor element.

The two junction alumina coated thermocouple similar to that used in Example 1 was (three times) sequentially dipped in a solution of 1.0 g titanium isopropoxide and 1.0 g hexane, blotted, soaked in hexane, blotted, dried in an oven at 125° C. for 45 minutes, and calcined in air at 300° C. for one hour. The thermocouple was then recalcined at 500° C.

One junction of the thermocouple was then dipped in an iron salt solution (1.52 g $Fe(NO_3)_3$ per 1 g $H_2O$), soaked for 15 seconds, blotted, dried at 140° C. for 30 minutes, and calcined at 500° C. The reference junction was coated with alundum in a similar fashion.

This sensor was tested in the manner described above with relation to FIG. 5 and exhibited the same plateau on the temperature-sensor output graph.

This invention has been disclosed both by description and by example. The examples are just examples and should not be used to limit the scope of the invention here claimed in any way. Additionally, it will be apparent to a reader having ordinary skill in this art that the variations and equivalents will be apparent operate in the same way in measuring $NO_x$ and yet be within the spirit of these claims.

We claim as our invention:

1. A device for measuring various nitrogen oxides ($NO_x$) concentration in a flowing gas stream comprising:
   a. a catalytic sensor element comprising a catalyst for reducing $NO_x$ to $N_2$ in the presence of a $NO_x$ reductant which catalyst is coated upon a temperature measuring device, where the catalyst and temperature measuring device are situated so that the catalytic contacts the flowing gas stream, and the heat produced by reducing $NO_x$ raises the temperature of the temperature measuring device substantially proportional to the $NO_x$ concentration in the flowing gas stream;
   b. a reference element for detecting the ambient temperature of the flowing gas stream in the vicinity of the catalytic sensor element;
   c. a $NO_x$ reductant source introducing $NO_x$ reductant into the flowing gas stream for contact with the catalytic sensor element; and
   d. a flowing gas stream temperature controller for controlling the temperature of the flowing gas stream prior to its passage over the catalytic sensor element to operating temperature.

2. The device of claim 1 where the temperature measuring device of the catalytic sensor element is a resistance temperature device (RTD).

3. The device of claim 1 where the temperature measuring device of the catalytic sensor device is a thermistor.

4. The device of claim 1 where the temperature measuring device of the catalytic sensor element is a thermocouple.

5. The device of claim 1 where the catalyst comprises a metal selected from the group consisting of Group V and Group VIII transition metals.

6. The device of claim 5 where the catalyst comprises vanadium.

7. The device of claim 1 where the reference element comprises a resistance temperature device (RTD).

8. The device of claim 1 where the reference element comprises a thermistor.

9. The device of claim 1 where the reference element comprises a thermocouple.

10. The device of claim 1 where the reference element is a resistor.

11. The device of claim 1 where the $NO_x$ reductant source is a source comprising a $NO_2$ reductant selected from the group consisting of ammonia, cyanuric acid, urea, ammonium carbonate, ammonium carbamate, ethyl carbamate, and gaseous amines.

12. The device of claim 11 where the reductant is ammonia.

13. The device of claim 1 where the flowing gas temperature controller comprises a heat exchanger.

14. A process for measuring various nitrogen oxides ($NO_x$) in a flowing gas stream comprising the steps of:
  a. introducing a $NO_x$ reductant into the flowing gas stream containing $NO_x$ to produce a mixed stream,
  b. controlling the temperature of the flowing gas stream to an appropriate operating temperature, and
  c. passing the mixed stream to a catalytic sensor comprising a catalyst for reducing $NO_x$ to $N_2$ with the $NO_x$ reductant upon contacting the mixed stream and a temperature measuring device where the catalyst and temperature measuring device are situated so that the heat produced by reducing $NO_x$ with the catalyst raises the temperature of the temperature measuring device substantially proportional to the $NO_x$ concentration in the mixed stream where the temperature measuring device provides a measurable output related to the temperature rise.

15. The process of claim 14 where the mixed stream additionally passes a reference element in close proximity to the catalytic sensor element which reference element comprises a temperature measuring device producing a measurable output related to the temperature of the mixed stream and of the same type as the measurable output of the catalytic sensor element.

16. The process of claim 14 where the flowing gas stream additionally comprises at least one of carbon monoxide (CO) and sulfur dioxide (SO2).

17. The process of claim 14 where the measurable output is voltage.

18. The process of claim 15 where the measurable output is resistance.

19. The process of claim 14 where the catalyst comprises a metal selected from the group consisting of Group V and Group VIII transition metals.

20. The process of claim 19 where the catalyst comprises vanadium.

21. The process of claim 19 where the $NO_x$ reductant is selected from the group consisting of ammonia, cyanuric acid, urea, ammonium carbonate, ammonium carbamate, ethyl carbamate, and gaseous amines.

22. The process of claim 21 where the $NO_x$ reductant is ammonia.

* * * * *